(12) United States Patent
Connelly et al.

(10) Patent No.: US 8,987,247 B2
(45) Date of Patent: Mar. 24, 2015

(54) MONOACYLGLYCEROL LIPASE INHIBITORS FOR THE TREATMENT OF METABOLIC DISEASES AND RELATED DISORDERS

(71) Applicant: Janssen Pharmaceutica NV, New Brunswick, NJ (US)

(72) Inventors: Margery Connelly, Lansdale, PA (US); Christopher M. Flores, Lansdale, PA (US); Mark J. Macielag, Gwynedd Valley, PA (US)

(73) Assignee: Janssen Pharmaceutica NV, Beerse (BE)

( * ) Notice: Subject to any disclaimer, the term of this patent is extended or adjusted under 35 U.S.C. 154(b) by 134 days.

(21) Appl. No.: 13/628,428

(22) Filed: Sep. 27, 2012

(65) Prior Publication Data

US 2013/0085129 A1 Apr. 4, 2013

Related U.S. Application Data

(60) Provisional application No. 61/541,394, filed on Sep. 30, 2011.

(51) Int. Cl.
*A01N 43/00* (2006.01)
*A61K 31/397* (2006.01)
*A61K 31/496* (2006.01)

(52) U.S. Cl.
CPC .............. *A61K 31/496* (2013.01); *Y10S 514/91* (2013.01); *Y10S 514/911* (2013.01)
USPC ............ 514/210.01; 514/210.17; 514/210.18; 514/210.19; 514/910; 514/911

(58) Field of Classification Search
USPC ...................... 514/210.18, 910, 911
See application file for complete search history.

(56) References Cited

U.S. PATENT DOCUMENTS

2010/0324014 A1* 12/2010 Bian et al. ................. 514/210.18

FOREIGN PATENT DOCUMENTS

| WO | WO 2008/145843 A | | 12/2008 | | |
|---|---|---|---|---|---|
| WO | WO 2009/117444 A | | 9/2009 | | |
| WO | WO 2010/124082 A | | 10/2010 | | |
| WO | WO 2010124112 A1 | * | 10/2010 | ........... | A61K 31/496 |
| WO | WO 2010124122 A1 | * | 10/2010 | | |

OTHER PUBLICATIONS

Taschler et al., (Journal of Biological Chemistry vol. 286, pp. 17467-17477, published online Mar. 23, 2011).*
Taschler, U. et al., Journal of Biological Chemistry vol. 286, pp. 17467-17477. Published online Mar. 23, 2011.*
Barba et al., "Appropriate body-mass index for Asian populations and its implications for policy and intervention strategies.", The Lancet, 2004, pp. 157-162, vol. 363.
Wall et al., "A novel poxvirus gene and its human homolog are similar to an *E. coli* lysophospholipaase.", Virus Res., 1997, pp. 152-167, vol. 52.
Dinh et al., "Brain monoglyceride lipase participating in endocannabinoid inactivation.", Proc. Nat. Acad. Sci., 2002, pp. 10819-10824, vol. 99.
Schlossburg et al., "Chronic monoacylglycerol lipase blockade causes functional antagonism of the endocannabinoid system.", Nat. Neurosci., 2010, pp. 1113-1119, vol. 13(9).
Chon et al., "Over-expression of monoacylglycerol lipase (MGL) in mouse small intestine results in an obese phenotype.", FASEB, 2008, pp. 807.12, vol. 22.
Taschler et al., "Monoglyceride Lipase-deficiency in Mice Impairs Lipolysis and Attenuates Diet-Induced Insuline Resistance.", JBC, 2011, pp. 17467-17477, vol. 286(20).
Pantoliano et al., "High Density Miniaturized Thermal Shift Assays as a General Strategy for Drug Discovery.", Journal of Biomolecular Screening, 2001, pp. 429-440, vol. 6(6).
Matulis et al., "Thermodynamic Stability of Carbonic Anhydrase: Measurements of Binding Affinity and Stoichiometry Using ThermoFluor.", Biochemistry, 2005, vol. 44, pp. 5258-5266.
Buettner et al., "High-fat diets: modeling the metabolic disorders of human obesity in Rodents.", Obesity, 2007, pp. 798-808, vol. 15.
Van Heek et al., "Diet-induced obese mice develop peripheral, but not central, resistance to lepton.", J Clin Invest, 1997, pp. 385-390, vol. 99.
Winzell, M., "The High-fat Diet-Fed Mouse: A Model for Studying Mechanisms and Treatment of Impaired Glucose Tolerance and Type 2 Diabetes.", Diabetes, Dec. 2004, pp. S215-S219, vol. 53(3).

* cited by examiner

*Primary Examiner* — Paul Zarek
*Assistant Examiner* — George W Kosturko
(74) *Attorney, Agent, or Firm* — Thomas Dodd

(57) ABSTRACT

Disclosed are compounds, compositions and methods for treating metabolic diseases, including obesity and diabetes, and for reducing weight gain. Such compounds are represented by formula (I) as follows:

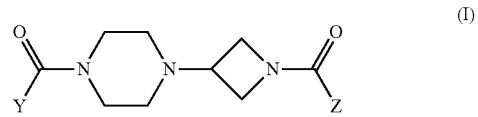

wherein Y and Z are defined herein.

2 Claims, No Drawings

MONOACYLGLYCEROL LIPASE INHIBITORS FOR THE TREATMENT OF METABOLIC DISEASES AND RELATED DISORDERS

CROSS-REFERENCE TO RELATED APPLICATIONS

This application claims priority to U.S. provisional patent application No. 61/541,394, filed Sep. 30, 2011, which is hereby incorporated by reference in its entirety.

STATEMENT REGARDING FEDERALLY SPONSORED RESEARCH OR DEVELOPMENT

The research and development of the invention described below was not federally sponsored.

BACKGROUND OF THE INVENTION

Monoglyceride Lipase (MGL) is a target known in the art and first identified by Wall et al. (*Virus Res.* 1997, 52, 152-167) in 1997 and designated HUKS. Dinh et al. (*Proc. Nat. Acad. Sci.,* 2002, 99, 10819-10824) found that the rat MGL participates in inactivation of 2-arachidonoylglycerol (2-AG), an endogenous cannabinoid monoglyceride. It is highly expressed in regions of rat brain that also express cannabinoid receptors and it appears to assume a presynaptic localization in the hippocampus. Adenovirus-mediated transfer of MGL cDNA into rat cortical neurons increased MGL expression and attenuated 2-AG accumulation induced by N-methyl-D-aspartate/carbachol. MGL inhibitors, on the other hand, have been shown by Schlossburg et al (*Nat. Neurosci.,* 2010, Sep. 13(9), 1113-9) to enhance the signaling of the endocannabinoid system by elevating the level of 2-AG, the endocannabinoid of highest abundance in the central nervous system (CNS) and gastrointestinal tract. For this reason, MGL inhibitors are potentially useful for the treatment of pain, inflammation, and CNS disorders.

In addition to the brain, MGL is expressed in adipocytes, where it functions together with hormone-sensitive lipase (LIPE) to hydrolyze intracellular triglyceride stores, and in the intestine, where it is largely responsible for cleaving monoacyglycerols to form free fatty acids and glycerol. It has been observed by Chon, et al. (*FASEB,* 2008, 22, 807-12) that increased expression of MGL in the intestine causes an obese phenotype, most likely due to hyperphagia (overeating). Further evidence from MGL knockout mice ("MGL-ko mice") (Taschler, et al. *JBC,* 2011, 286(20), 17467-77) showed that MGL-deficiency results in accumulation of 2-AG and other MG species in various tissues, including brain, adipose and liver. Fasted MGL-ko mice exhibited reduced plasma glycerol and triacylglycerol, as well as liver triacylglycerol levels indicative of impaired lipolysis. MGL-ko mice receiving a high-fat diet showed significantly improved glucose tolerance and insulin sensitivity in comparison to wild-type controls. These observations implicate MGL in metabolic diseases and suggest that MGL inhibitors will have beneficial effects on metabolic disorders, including obesity, hyperphagia and diabetes.

It is an object of the present invention to provide MGL inhibitors. It is also an object of the invention to provide a method of treating, ameliorating or preventing metabolic disorders, such as obesity, hyperphagia and diabetes, by the administration of a compound of formula (I). It is also an object of the invention to provide a method of reducing food consumption and/or weight gain of a subject, by the administration of a compound of formula (I). And, it is an object of the invention to provide a pharmaceutical composition comprising a compound of formula (I), useful for treating, ameliorating or preventing metabolic disorders.

SUMMARY OF THE INVENTION

The present invention is directed to a method for treating, ameliorating, or preventing metabolic diseases; comprising, consisting of, and/or consisting essentially of administering to a subject in need thereof, a therapeutically effective amount of a compound of formula (I)

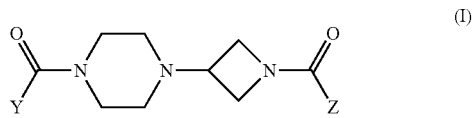

or an enantiomer, diastereomer, solvate, or pharmaceutically acceptable salt thereof;
wherein:
Y is a heteroaryl selected from the group consisting of thienyl, furanyl, thiazolyl, isothiazolyl, oxazolyl, pyrrolyl, isoxazolyl, triazolyl, and [1,2,3]thiadiazolyl;
wherein Y is optionally substituted with one substituent selected from the group consisting of fluoro, chloro, bromo, $C_{1-4}$alkyl, cyano, and trifluoromethyl;
Z is a heteroaryl selected from the group consisting of indolyl, indazolyl, benzoxazolyl, benzothiazolyl, benzofuranyl, benzothienyl, 1H-pyrrolo[3,2-b]pyridin-5-yl, 1H-thieno[2,3-c]pyrazol-5-yl, 1H-pyrrolo[2,3-b]pyridin-5-yl, 1H-pyrazolo[3,4-b]pyridin-5-yl, furo[2,3-b]pyridin-2-yl, quinazolinyl, and benzimidazolyl;
wherein Z is optionally independently substituted with one to two substitutents selected from the group consisting of chloro, fluoro, $C_{1-4}$alkyl, $C_{1-4}$alkoxy, and trifluoromethyl; and Z is substituted with one additional substituent that is
(i) phenyl or
(ii) a heteroaryl selected from the group consisting of pyrimidinyl, thienyl, quinolinyl, pyridinyl, isoxazolyl, thiazolyl, benzimidazolyl, pyrrolyl, furanyl, pyrimidinyl, and pyrazolyl;
and wherein said phenyl and heteroaryl substituents of Z are optionally independently substituted with one to two substituents selected from the group consisting of $C_{1-4}$alkyl; $C_{1-4}$alkoxy; one to three fluoro or chloro substituents; trifluoromethyl; trifluoromethoxy; cyano; carboxy; aminocarbonyl; formyl; nitro; bromo; hydroxy; and $C_{1-4}$alkylsulfonyl;
with the proviso that a compound of formula (I) is other than a compound wherein Y is thiazol-2-yl and Z is 5-(2-fluoropyridin-3-yl)-1H-benzimidazol-2-yl.

The present invention is further directed to the use of a compound of formula (I) as herein defined for the preparation of a medicament or a pharmaceutical composition for the treatment, amelioration and/or prevention of metabolic diseases, including obesity, hyperphagia, and diabetes, in a subject in need thereof.

The present invention is further directed to the use of a compound of formula (I) as herein defined for the preparation of a medicament or a pharmaceutical composition for reducing food consumption and/or weight gain in a subject in need thereof.

DETAILED DESCRIPTION OF THE INVENTION

As used herein, the following terms are intended to have the following meanings:

With reference to substituents, the term "independently" refers to the situation that when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g., $C_{1-8}$) refer independently to the number of carbon atoms in an alkyl moiety or to the alkyl portion of a larger alkyl-containing substituent. In substituent groups with multiple alkyl groups such as $(C_{1-6}alkyl)_2$-amino- the $C_{1-6}$alkyl groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 or more carbon atoms, wherein an alkenyl chain contains at least one double bond and an alkynyl chain contains at least one triple bond.

The term "aryl" refers to an unsaturated, aromatic monocyclic or bicyclic ring of 6 to 10 carbon members. Examples of aryl rings include phenyl and naphthalenyl.

The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen, or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. When a heteroaryl is bicyclic, at least one heteroatom is present in at least one ring. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolyl, indazolyl, benzoxazolyl, benzothiazolyl, benzofuranyl, and benzothienyl. Unless otherwise noted, the heteroaryl is attached to its pendant group at any heteroatom or carbon atom that results in a stable structure.

The term "halogen" or "halo" refers to fluorine, chlorine, bromine and iodine.

The term "oxo" refers to the group (═O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as subcombinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

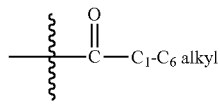

The term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of 2 enantiomers. Compounds containing 2 stereocenters both drawn without stereo bond designations are a mixture of 4 diastereomers. Compounds with 2 stereocenters both labeled "RS" and drawn with stereo bond designations are a 2-component mixture with relative stereochemistry as drawn. Compounds with 2 stereocenters both labeled "*RS" and drawn with stereo bond designations are a 2-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of formula (I) can be selected by one of ordinary skill in the art to provide compounds that are chemically stable and that can be readily synthesized by techniques known in the art as well as those methods set forth herein.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The term "composition" is intended to encompass a product comprising the specified ingredients in therapeutically effective amounts, as well as any product that results, directly or indirectly, from combinations of the specified ingredients in the specified amounts.

The terms "treating", "treatment", "ameliorating" and the like, as used herein, unless otherwise noted, include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, syndrome, or disorder.

The terms "preventing" and "prevention" as used herein, unless otherwise noted, include (a) reduction in the frequency of one or more symptoms; (b) reduction in the severity of one or more symptoms; (c) the delay or avoidance of the development of additional symptoms; and/or (d) delay or avoidance of the development of the disease, disorder, syndrome, or condition.

One skilled in the art will recognize that where the present invention is directed to methods of prevention, a subject in need of thereof (i.e., a subject in need of prevention) includes any subject (preferably a mammal, more preferably a human) who has experienced or exhibited at least one symptom of the disorder, disease, syndrome, or condition to be prevented. Further, a subject in need thereof may additionally be a subject (preferably a mammal, more preferably a human) who has not exhibited any symptoms of the disorder, disease, syndrome, or condition to be prevented, but who has been deemed by a physician, clinician, or other medical professional to be at risk of developing said disorder, disease, syndrome, or condition. For example, the subject may be deemed at risk of developing a disorder, disease, syndrome, or condition (and therefore in need of prevention or preventive treatment) as a consequence of the subject's medical history, including, but not limited to, family history, pre-disposition, co-existing (comorbid) disorders or conditions, genetic testing, and the like.

The term "MGL inhibitor" is intended to encompass a compound that interacts with MGL to substantially reduce or eliminate its catalytic activity, thereby increasing the concentrations of its substrate(s).

The term "MGL-modulated" is used to refer to the condition of being affected by the modulation of the MGL enzyme including the condition of being affected by the inhibition of the MGL enzyme, such as, for example, metabolic diseases including obesity and diabetes The terms "affect" or "affected" (when referring to a disease, syndrome, condition or disorder that is affected by inhibition of MGL) as used herein, unless otherwise noted, implies a reduction in the frequency and/or severity of one or more symptoms or manifestations of said disease, syndrome, condition or disorder; and/or imply the prevention of the development of one or more symptoms or manifestations of said disease, syndrome, condition or disorder or the development of the disease, condition, syndrome or disorder.

Compounds of formula (I) are useful in methods for treating, ameliorating and/or preventing metabolic diseases or a disorder that causes such diseases by the inhibition of MGL. Such methods comprise, consist of and/or consist essentially of administering to a subject, including an animal, a mammal, and a human in need of such treatment, amelioration and/or prevention, a therapeutically effective amount of a compound of formula (I) or a solvate or pharmaceutically acceptable salt thereof. More particularly, a compound of formula (I) is useful for treating, ameliorating and/or preventing metabolic diseases, such as obesity, hyperphagia, and diabetes, comprising administering to a subject in need thereof a therapeutically effective amount of a compound of formula (I), as herein defined. Furthermore, a compound of formula (I) is useful for reducing weight gain of a subject, comprising administering to the subject a therapeutically effective amount of a compound of formula (I), as herein defined.

Examples of metabolic disorder, syndrome, diseases or conditions include, but are not limited to, diabetes, hyperphagia, overweight, obesity, obesity-associated insulin resistance, atherosclerosis, and associated symptoms or complications thereof. They also include such conditions as IDDM (insulin-dependent diabetes mellitus), NIDDM (non insulin-dependent diabetes mellitus), IGT (Impaired Glucose Tolerance), IFG (Impaired Fasting Glucose), Syndrome X (i.e., Metabolic Syndrome), hyperglycemia, elevated blood glucose level, and insulin resistance. "Prediabetic condition" or "prediabetic state" include IGT and IFG.

The term "obesity" refers to a condition in which there is an excess of body fat. The operational definition of obesity is often based on the Body Mass Index (BMI), which is calculated as body weight per height in meters squared ($kg/m^2$). An "obese subject" is an otherwise healthy subject with a Body Mass Index (BMI) greater than or equal to 30 kg/m2 or a subject having at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject having at least one co-morbidity with a BMI of 25 $kg/m^2$ to less than 27 $kg/m^2$.

The increased risks associated with obesity occur at a lower BMI in Asian populations (Barba, et al. *The Lancet,* 2004, 363, 157-162). In Asian countries, the available data do not indicate one clear BMI cut-off point for all populations for overweight or obesity individuals. In Japan, "obesity" refers to a condition whereby a subject with at least one obesity-induced or obesity-related co-morbidity, that requires weight reduction or that would be improved by weight reduction, has a BMI greater than or equal to 25 $kg/m^2$. As another example in Asia-Pacific Island populations such as Indonesia and Singapore, a "subject at risk of obesity" is a subject with a BMI of greater than 23 $kg/m^2$ to less than 25 $kg/m^2$.

The term "obesity" as used herein, unless otherwise noted, is meant to encompass all of the above definitions of obesity.

Obesity-induced or obesity-related co-morbidities include, but are not limited to, diabetes, impaired glucose tolerance, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders, diseases, syndromes, and conditions refer to the administration of at least one compound of the present invention for the reduction of or maintenance of the body weight of an obese subject.

In an embodiment, the present invention is directed to a method for treating, ameliorating, or preventing metabolic disorders, diseases, syndromes, and conditions; comprising, consisting of, and/or consisting essentially of administering to a subject in need thereof, a therapeutically effective amount of a compound of formula (I)

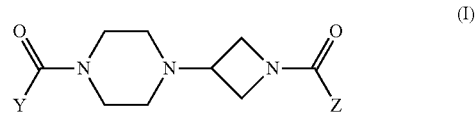

(I)

or an enantiomer, diastereomer, solvate, or pharmaceutically acceptable salt thereof;

wherein:
a) Y is a heteroaryl selected from the group consisting of thienyl, furanyl, thiazolyl, isothiazolyl, oxazolyl, pyrrolyl, isoxazolyl, and [1,2,3]thiadiazolyl;
wherein Y is optionally substituted with one substituent selected from the group consisting of fluoro, chloro, bromo, $C_{1-4}$alkyl, and trifluoromethyl;
b) Y is a heteroaryl selected from the group consisting of thienyl, furanyl, thiazolyl, isothiazolyl, oxazolyl, pyrrolyl, and isoxazolyl;
wherein Y is optionally substituted with one substituent selected from the group consisting of fluoro, chloro, bromo, and trifluoromethyl;
c) Z is a heteroaryl selected from the group consisting of indolyl, indazolyl, benzoxazolyl, benzothiazolyl, benzofuranyl, benzothienyl, 1H-pyrrolo[3,2-b]pyridin-5-yl, 1H-thieno[2,3-c]pyrazol-5-yl, 1H-pyrrolo[2,3-b]pyridin-5-yl, 1H-pyrazolo[3,4-b]pyridin-5-yl, furo[2,3-b]pyridin-2-yl, quinazolinyl, and benzimidazolyl;
wherein Z is optionally independently substituted with one to two substituents selected from the group consisting of chloro, fluoro, $C_{1-4}$alkyl, $C_{1-4}$alkoxy, and trifluoromethyl; and Z is substituted with one additional substituent that is
(i) phenyl or
(ii) a heteroaryl selected from the group consisting of thienyl, quinolinyl, pyridinyl, isoxazolyl, benzimidazolyl, furanyl, pyrimidinyl, and pyrazolyl;
and wherein said phenyl and heteroaryl substituents of Z are optionally independently substituted with one to two substituents selected from the group consisting of $C_{1-4}$alkyl; $C_{1-4}$alkoxy; one to three fluoro or chloro substituents; trifluoromethyl; trifluoromethoxy; cyano; carboxy; aminocarbonyl; formyl; nitro; bromo; hydroxy; and $C_{1-4}$alkylsulfonyl;
d) Z is a heteroaryl selected from the group consisting of indazolyl, benzoxazolyl, benzothiazolyl, benzofuranyl, benzothienyl, 1H-pyrrolo[3,2-b]pyridin-5-yl, 1H-thieno[2,3-c]pyrazol-5-yl, 1H-pyrrolo[2,3-b]pyridin-5-yl, quinazolinyl, and benzimidazolyl;
wherein Z is optionally independently substituted with one to two substituents selected from the group consisting of chloro, fluoro, $C_{1-4}$alkyl, $C_{1-4}$alkoxy, and trifluoromethyl; and Z is substituted with one additional substituent that is
(i) phenyl or
(ii) a heteroaryl selected from the group consisting of pyrimidinyl, thienyl, quinolinyl, pyridinyl, pyrimidinyl, and pyrazolyl;
and wherein said phenyl and heteroaryl substituents of Z are optionally independently substituted with one to two substituents selected from the group consisting of $C_{1-4}$alkyl; $C_{1-4}$alkoxy; one to three fluoro or chloro substituents; trifluoromethyl; trifluoromethoxy; cyano; carboxy; aminocarbonyl; formyl; nitro; bromo; hydroxy; and $C_{1-4}$alkylsulfonyl;
and combinations of a) through d) above;
with the proviso that a compound of formula (I) is other than a compound wherein Y is thiazol-2-yl and Z is 5-(2-fluoropyridin-3-yl)-1H-benzimidazol-2-yl.

In an embodiment, the present invention is directed to a method for treating, ameliorating, or preventing metabolic disorders, diseases, syndromes, and conditions; comprising, consisting of, and/or consisting essentially of administering to a subject in need thereof, a therapeutically effective amount of a compound of formula (I)

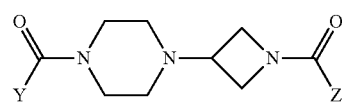

or an enantiomer, diastereomer, solvate, or pharmaceutically acceptable salt thereof;
wherein:
Y is a heteroaryl selected from the group consisting of thienyl, furanyl, thiazolyl, isothiazolyl, oxazolyl, pyrrolyl, isoxazolyl, and [1,2,3]thiadiazolyl;
wherein Y is optionally substituted with one substituent selected from the group consisting of fluoro, chloro, bromo, $C_{1-4}$alkyl, and trifluoromethyl;
Z is a heteroaryl selected from the group consisting of indolyl, indazolyl, benzoxazolyl, benzothiazolyl, benzofuranyl, benzothienyl, 1H-pyrrolo[3,2-b]pyridin-5-yl, 1H-thieno[2,3-c]pyrazol-5-yl, 1H-pyrrolo[2,3-b]pyridin-5-yl, 1H-pyrazolo[3,4-b]pyridin-5-yl, furo[2,3-b]pyridin-2-yl, quinazolinyl, and benzimidazolyl;
wherein Z is optionally independently substituted with one to two substituents selected from the group consisting of chloro, fluoro, $C_{1-4}$alkyl, $C_{1-4}$alkoxy, and trifluoromethyl; and Z is substituted with one additional substituent that is
(i) phenyl or
(ii) a heteroaryl selected from the group consisting of thienyl, quinolinyl, pyridinyl, isoxazolyl, benzimidazolyl, furanyl, pyrimidinyl, and pyrazolyl;
and wherein said phenyl and heteroaryl substituents of Z are optionally independently substituted with one to two substituents selected from the group consisting of $C_{1-4}$alkyl; $C_{1-4}$alkoxy; one to three fluoro or chloro substituents; trifluoromethyl; trifluoromethoxy; cyano; carboxy; aminocarbonyl; formyl; nitro; bromo; hydroxy; and $C_{1-4}$alkylsulfonyl;
with the proviso that a compound of formula (I) is other than a compound wherein Y is thiazol-2-yl and Z is 5-(2-fluoropyridin-3-yl)-1H-benzimidazol-2-yl.

In an embodiment, the present invention is directed to a method for treating, ameliorating, or preventing metabolic disorders, diseases, syndromes, and conditions; comprising, consisting of, and/or consisting essentially of administering to a subject in need thereof, a therapeutically effective amount of a compound of formula (I)

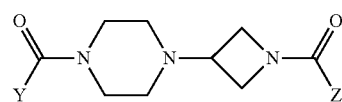

or an enantiomer, diastereomer, solvate, or pharmaceutically acceptable salt thereof;
wherein:
Y is a heteroaryl selected from the group consisting of heteroaryl selected from the group consisting of thienyl, furanyl, thiazolyl, isothiazolyl, oxazolyl, pyrrolyl, and isoxazolyl;
wherein Y is optionally substituted with one substituent selected from the group consisting of fluoro, chloro, bromo, and trifluoromethyl;
Z is a heteroaryl selected from the group consisting of indazolyl, benzoxazolyl, benzothiazolyl, benzofuranyl, benzothienyl, 1H-pyrrolo[3,2-b]pyridin-5-yl, 1H-thieno[2,3-c]pyrazol-5-yl, 1H-pyrrolo[2,3-b]pyridin-5-yl, quinazolinyl, and benzimidazolyl;

wherein Z is optionally independently substituted with one to two substitutents selected from the group consisting of chloro, fluoro, $C_{1-4}$alkyl, $C_{1-4}$alkoxy, and trifluoromethyl; and Z is substituted with one additional substituent that is (i) phenyl or (ii) a heteroaryl selected from the group consisting of pyrimidinyl, thienyl, quinolinyl, pyridinyl, pyrimidinyl, and pyrazolyl;

and wherein said phenyl and heteroaryl substituents of Z are optionally independently substituted with one to two substituents selected from the group consisting of $C_{1-4}$alkyl; $C_{1-4}$alkoxy; one to three fluoro or chloro substituents; trifluoromethyl; trifluoromethoxy; cyano; carboxy; aminocarbonyl; formyl; nitro; bromo; hydroxy; and $C_{1-4}$alkylsulfonyl;

with the proviso that a compound of formula (I) is other than a compound wherein Y is thiazol-2-yl and Z is 5-(2-fluoropyridin-3-yl)-1H-benzimidazol-2-yl.

An embodiment of the present invention is directed to a method for treating, ameliorating, or preventing metabolic disorders, diseases, syndromes, and conditions, including obesity and diabetes; comprising, consisting of, and/or consisting essentially of administering to a subject in need thereof, a therapeutically effective amount of 1-(1-{[3-chloro-6-(trifluoromethyl)-1-benzothiophen-2-yl]carbonyl}azetidin-3-yl)-4-(1,3-thiazol-4-ylcarbonyl)piperazine (Compound 1);

Compound 1

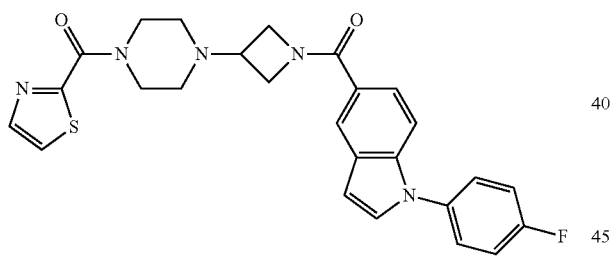

or a solvate or pharmaceutically acceptable salt thereof.

In an embodiment, the present invention is directed to a method for reducing food consumption and/or weight gain of a subject comprising, consisting of, and/or consisting essentially of administering to the subject in need thereof, a therapeutically effective amount of a compound of formula (I)

(I)

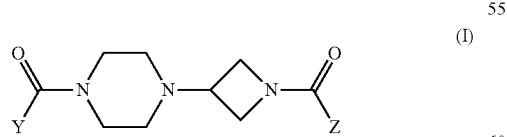

or an enantiomer, diastereomer, solvate, or pharmaceutically acceptable salt thereof;
wherein:
a) Y is a heteroaryl selected from the group consisting of thienyl, furanyl, thiazolyl, isothiazolyl, oxazolyl, pyrrolyl, isoxazolyl, and [1,2,3]thiadiazolyl;

wherein Y is optionally substituted with one substituent selected from the group consisting of fluoro, chloro, bromo, $C_{1-4}$alkyl, and trifluoromethyl;

b) Y is a heteroaryl selected from the group consisting of thienyl, furanyl, thiazolyl, isothiazolyl, oxazolyl, pyrrolyl, and isoxazolyl;

wherein Y is optionally substituted with one substituent selected from the group consisting of fluoro, chloro, bromo, and trifluoromethyl;

c) Z is a heteroaryl selected from the group consisting of indolyl, indazolyl, benzoxazolyl, benzothiazolyl, benzofuranyl, benzothienyl, 1H-pyrrolo[3,2-b]pyridin-5-yl, 1H-thieno[2,3-c]pyrazol-5-yl, 1H-pyrrolo[2,3-b]pyridin-5-yl, 1H-pyrazolo[3,4-b]pyridin-5-yl, furo[2,3-b]pyridin-2-yl, quinazolinyl, and benzimidazolyl;

wherein Z is optionally independently substituted with one to two substitutents selected from the group consisting of chloro, fluoro, $C_{1-4}$alkyl, $C_{1-4}$alkoxy, and trifluoromethyl; and Z is substituted with one additional substituent that is (i) phenyl or (ii) a heteroaryl selected from the group consisting of thienyl, quinolinyl, pyridinyl, isoxazolyl, benzimidazolyl, furanyl, pyrimidinyl, and pyrazolyl;

and wherein said phenyl and heteroaryl substituents of Z are optionally independently substituted with one to two substituents selected from the group consisting of $C_{1-4}$alkyl; $C_{1-4}$alkoxy; one to three fluoro or chloro substituents; trifluoromethyl; trifluoromethoxy; cyano; carboxy; aminocarbonyl; formyl; nitro; bromo; hydroxy; and $C_{1-4}$alkylsulfonyl;

d) Z is a heteroaryl selected from the group consisting of indazolyl, benzoxazolyl, benzothiazolyl, benzofuranyl, benzothienyl, 1H-pyrrolo[3,2-b]pyridin-5-yl, 1H-thieno[2,3-c]pyrazol-5-yl, 1H-pyrrolo[2,3-b]pyridin-5-yl, quinazolinyl, and benzimidazolyl;

wherein Z is optionally independently substituted with one to two substitutents selected from the group consisting of chloro, fluoro, $C_{1-4}$alkyl, $C_{1-4}$alkoxy, and trifluoromethyl; and Z is substituted with one additional substituent that is (i) phenyl or (ii) a heteroaryl selected from the group consisting of pyrimidinyl, thienyl, quinolinyl, pyridinyl, pyrimidinyl, and pyrazolyl;

and wherein said phenyl and heteroaryl substituents of Z are optionally independently substituted with one to two substituents selected from the group consisting of $C_{1-4}$alkyl; $C_{1-4}$alkoxy; one to three fluoro or chloro substituents; trifluoromethyl; trifluoromethoxy; cyano; carboxy; aminocarbonyl; formyl; nitro; bromo; hydroxy; and $C_{1-4}$alkylsulfonyl;

and combinations of a) through d) above;

with the proviso that a compound of formula (I) is other than a compound wherein Y is thiazol-2-yl and Z is 5-(2-fluoropyridin-3-yl)-1H-benzimidazol-2-yl.

In an embodiment, the present invention is directed to a method for reducing food consumption and/or weight gain of a subject comprising, consisting of, and/or consisting essentially of administering to a subject in need thereof, a therapeutically effective amount of a compound of formula (I)

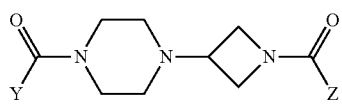

or an enantiomer, diastereomer, solvate, or pharmaceutically acceptable salt thereof;
wherein:
  Y is a heteroaryl selected from the group consisting of thienyl, furanyl, thiazolyl, isothiazolyl, oxazolyl, pyrrolyl, isoxazolyl, and [1,2,3]thiadiazolyl;
  wherein Y is optionally substituted with one substituent selected from the group consisting of fluoro, chloro, bromo, $C_{1-4}$alkyl, and trifluoromethyl;
  Z is a heteroaryl selected from the group consisting of indolyl, indazolyl, benzoxazolyl, benzothiazolyl, benzofuranyl, benzothienyl, 1H-pyrrolo[3,2-b]pyridin-5-yl, 1H-thieno[2,3-c]pyrazol-5-yl, 1H-pyrrolo[2,3-b]pyridin-5-yl, 1H-pyrazolo[3,4-b]pyridin-5-yl, furo[2,3-b]pyridin-2-yl, quinazolinyl, and benzimidazolyl;
  wherein Z is optionally independently substituted with one to two substitutents selected from the group consisting of chloro, fluoro, $C_{1-4}$alkyl, $C_{1-4}$alkoxy, and trifluoromethyl; and Z is substituted with one additional substituent that is
  (i) phenyl or
  (ii) a heteroaryl selected from the group consisting of thienyl, quinolinyl, pyridinyl, isoxazolyl, benzimidazolyl, furanyl, pyrimidinyl, and pyrazolyl;
  and wherein said phenyl and heteroaryl substituents of Z are optionally independently substituted with one to two substituents selected from the group consisting of $C_{1-4}$alkyl; $C_{1-4}$alkoxy; one to three fluoro or chloro substituents; trifluoromethyl; trifluoromethoxy; cyano; carboxy; aminocarbonyl; formyl; nitro; bromo; hydroxy; and $C_{1-4}$alkylsulfonyl;
  with the proviso that a compound of formula (I) is other than a compound wherein Y is thiazol-2-yl and Z is 5-(2-fluoropyridin-3-yl)-1H-benzimidazol-2-yl.

In an embodiment, the present invention is directed to a method for reducing food consumption and/or weight gain of a subject comprising, consisting of, and/or consisting essentially of administering to a subject in need thereof, a therapeutically effective amount of a compound of formula (I)

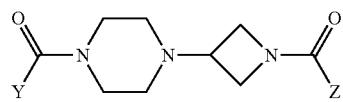

or an enantiomer, diastereomer, solvate, or pharmaceutically acceptable salt thereof;
wherein:
  Y is a heteroaryl selected from the group consisting of heteroaryl selected from the group consisting of thienyl, furanyl, thiazolyl, isothiazolyl, oxazolyl, pyrrolyl, and isoxazolyl;
  wherein Y is optionally substituted with one substituent selected from the group consisting of fluoro, chloro, bromo, and trifluoromethyl;
  Z is a heteroaryl selected from the group consisting of indazolyl, benzoxazolyl, benzothiazolyl, benzofuranyl, benzothienyl, 1H-pyrrolo[3,2-b]pyridin-5-yl, 1H-thieno[2,3-c]pyrazol-5-yl, 1H-pyrrolo[2,3-b]pyridin-5-yl, quinazolinyl, and benzimidazolyl;
  wherein Z is optionally independently substituted with one to two substitutents selected from the group consisting of chloro, fluoro, $C_{1-4}$alkyl, $C_{1-4}$alkoxy, and trifluoromethyl; and Z is substituted with one additional substituent that is
  (i) phenyl or
  (ii) a heteroaryl selected from the group consisting of pyrimidinyl, thienyl, quinolinyl, pyridinyl, pyrimidinyl, and pyrazolyl;
  and wherein said phenyl and heteroaryl substituents of Z are optionally independently substituted with one to two substituents selected from the group consisting of $C_{1-4}$alkyl; $C_{1-4}$alkoxy; one to three fluoro or chloro substituents; trifluoromethyl; trifluoromethoxy; cyano; carboxy; aminocarbonyl; formyl; nitro; bromo; hydroxy; and $C_{1-4}$alkylsulfonyl;
  with the proviso that a compound of formula (I) is other than a compound wherein Y is thiazol-2-yl and Z is 5-(2-fluoropyridin-3-yl)-1H-benzimidazol-2-yl.

In an embodiment, the present invention is directed to a method for reducing food consumption and/or weight gain of a subject comprising, consisting of, and/or consisting essentially of administering to a subject in need thereof, a therapeutically effective amount of

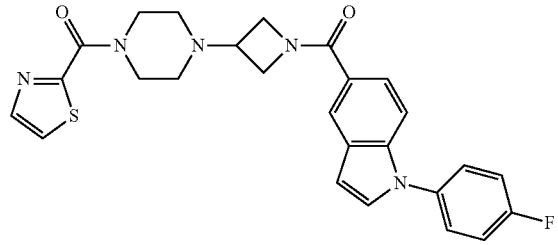

or a solvate or pharmaceutically acceptable salt thereof.

For use in medicine, salts of a compound of formula (I) refer to non-toxic "pharmaceutically acceptable salts." Other salts may, however, be useful in the preparation of a compound of formula (I) or of its pharmaceutically acceptable salts thereof. Suitable pharmaceutically acceptable salts of a compound of formula (I) include acid addition salts which can, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where a compound of formula (I) carries an acidic moiety, suitable pharmaceutically acceptable salts thereof may include alkali metal salts, such as sodium or potassium salts; alkaline earth metal salts, such as calcium or magnesium salts; and salts formed with suitable organic ligands, such as quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases that may be used in the preparation of pharmaceutically acceptable salts include acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxoglutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine and zinc hydroxide.

Embodiments of the present invention include prodrugs of a compound of formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Some of the crystalline forms for a compound of formula (I) may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of formula (I).

During any of the processes for preparation of a compound of formula (I) of the various embodiments of the present invention, it may be necessary and/or desirable to protect sensitive or reactive groups on any of the molecules concerned. This may be achieved by means of conventional protecting groups, such as those described in *Protective Groups in Organic Chemistry, Second Edition*, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis, Third Edition*, John Wiley & Sons, 1999. The protecting groups may be removed at a convenient subsequent stage using methods known from the art.

Even though a compound of formula (I) and the embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising a compound of formula (I) and at least one pharmaceutically acceptable carrier, pharmaceutically acceptable excipient, and/or pharmaceutically acceptable diluent.

By way of example, in the pharmaceutical compositions of embodiments of the present invention, a compound of formula (I) may be admixed with any suitable binder(s), lubricant(s), suspending agent(s), coating agent(s), solubilizing agent(s), and combinations thereof.

Solid oral dosage forms, such as tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, a compound of formula (I) can be administered by inhalation (intratracheal or intranasal) or in the form of a suppository or pessary, or it may be applied topically in the form of a lotion, solution, cream, ointment or dusting powder. For example, it can be incorporated into a cream comprising, consisting of, and/or consisting essentially of an aqueous emulsion of polyethylene glycols or liquid paraffin. It can also be incorporated, at a concentration of between about 1% and about 10% by weight of the cream, into an ointment comprising, consisting of, and/or consisting essentially of a white wax or white soft paraffin base together with any stabilizers and preservatives as may be required. An alternative means of administration includes transdermal administration by using a skin or transdermal patch.

The pharmaceutical compositions of the present invention (as well as a compound of formula (I) alone) can also be injected parenterally, for example intracavernosally, intravenously, intramuscularly, subcutaneously, intradermally or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing a compound of formula (I) as the active ingredient can be prepared by mixing a compound of formula (I) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus for liquid oral preparations, such as suspensions, syrups, elixirs and solutions, suitable carriers, excipients and diluents include water, glycols, oils, alcohols, flavoring agents, preservatives, stabilizers, coloring agents and the like; for solid oral preparations, such as powders, capsules and tablets, suitable carriers, excipients and diluents include starches, sugars, diluents, granulating agents, lubricants, binders, disintegrating agents and the like. Solid oral preparations also may be optionally coated with substances, such as, sugars, or be enterically-coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives, such as solubilizers and preservatives.

A therapeutically effective amount of a compound of formula (I) or a pharmaceutical composition thereof includes a dose range from about 0.1 mg to about 3000 mg, or any particular amount or range therein, in particular from about 1 mg to about 1000 mg, or any particular amount or range therein, or, more particularly, from about 10 mg to about 500 mg, or any particular amount or range therein, of active ingredient in a regimen of about 1 to about 4 times per day for an average (70 kg) human; although, it is apparent to one skilled in the art that the therapeutically effective amount for a compound of formula (I) will vary as will the diseases, syndromes, conditions, and disorders being treated.

For oral administration, a pharmaceutical composition is preferably provided in the form of tablets containing about 0.01, about 10, about 50, about 100, about 150, about 200, about 250, and about 500 milligrams of a compound of formula (I).

Advantageously, a compound of formula (I) may be administered in a single daily dose, or the total daily dosage may be administered in divided doses of two, three and four times daily.

Optimal dosages of a compound of formula (I) to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

A compound of formula (I) may be administered in any of the foregoing compositions and dosage regimens or by means of those compositions and dosage regimens established in the art whenever use of a compound of formula (I) is required for a subject in need thereof.

As an MGL inhibitor, a compound of formula (I) is useful in methods for treating and preventing a disease, a syndrome, a condition or a disorder in a subject, including an animal, a mammal and a human in which the disease, the syndrome, the condition or the disorder is affected by the modulation of the MGL enzyme. Such methods comprise, consist of and/or consist essentially of administering to a subject, including an animal, a mammal, and a human in need of such treatment or prevention a therapeutically effective amount of a compound of formula (I). In particular, a compound of formula (I) is useful for preventing or treating metabolic diseases, including obesity and diabetes. Furthermore, a compound of formula (I) is useful for reducing food consumption and/or weight gain.

General Synthetic Methods

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes. The various starting materials used in the schemes and examples are commercially available or may be prepared by methods well within the skill of persons versed in the art. The variables are as defined herein.

Abbreviations used in the instant specification, particularly the schemes and examples, are as follows:

aq. aqueous
CAN ceric ammonium nitrate
DCC N,N'-dicyclohexyl-carbodiimide
DCE 1,2-dichloroethane
DCM dichloromethane
DIAD diisopropyl azodicarboxylate
DIPEA diisopropyl-ethyl amine
DMF N,N-dimethylformamide
DMSO dimethylsulfoxide
DPPA diphenylphosphoryl azide
EDC   N-(3-dimethylaminopropyl)-N'-ethylcarbodiimide hydrochloride
ESI electrospray ionization
EtOAc ethyl acetate
EtOH ethanol
HATU   O-(1H-7-azabenzotriazol-1-yl)-1,1,3,3-tetramethyluronium hexafluorophosphate
HBTU O-(1H-benzotriazol-1-yl)-1,1,3,3-tetramethyluronium hexafluorophosphate
HEK human embryonic kidney
HOBt hydroxybenzotriazole
HPLC high performance liquid chromatography
mCPBA meta-chloroperoxybenzoic acid
MeCN acetonitrile
MeOH methanol
MeOTf methyl triflate
MHz megahertz
min minutes
MS mass spectrometry
NBS N-bromosuccinimide
NMR nuclear magnetic resonance
PyBrOP bromo-tris-pyrrolidinophosphonium hexafluorophosphate
RP reverse-phase
$R_t$ retention time
TEA/Et$_3$N triethylamine
TFA trifluoroacetic acid
THF tetrahydrofuran
TLC thin layer chromatography
TMS tetramethylsilane Scheme A illustrates a route for the synthesis compounds of formula (I), wherein Y and Z are as defined herein.

Scheme A

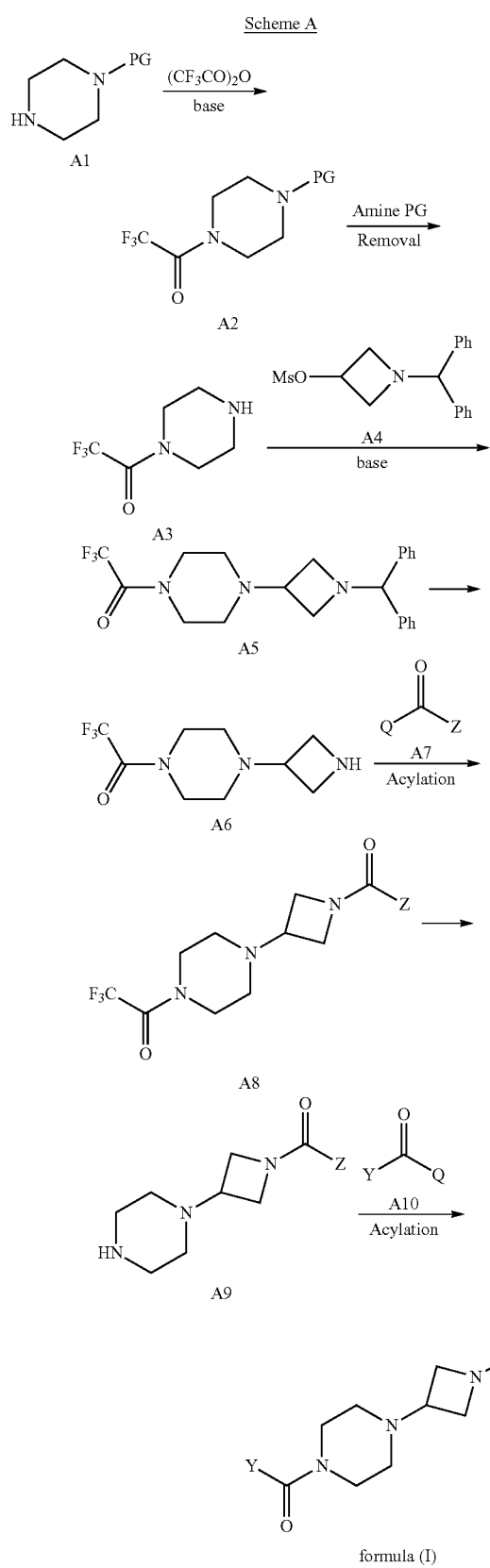

A compound of formula A1 wherein PG is a conventional amino protecting group such as, Boc, Fmoc, Cbz, and the like, is either commercially available or may be prepared by known methods described in the scientific literature. A compound of formula A1, in the presence of a non-nucleophilic base such as, pyridine, may be treated with trifluoroacetic anhydride to afford a compound of formula A2. Removal of the protecting group (PG) by conventional methods affords a compound of formula A3. A compound of formula A3 may be treated with a compound of formula A4 in the presence of a hindered amine base such as, DIPEA, to afford a compound of formula A5. Treatment of a compound of formula A5 with 1-chloroethyl chloroformate followed by methanolysis affords the corresponding amine of formula A6. A compound of formula A6 may be coupled with a carboxylic acid of formula A7 wherein Q is hydroxy, in the presence of an appropriate coupling agent such as, HATU, DCC, EDC, HBTU, PyBrOP, and the like; optionally in the presence of a base such as DIPEA, to afford an amide of formula A8. Similarly, an acid chloride of formula A7 wherein Q is chloro may be used to effect the acylation of a compound of formula A6. In such case a non-nucleophilic base such as pyridine may be added to afford an amide of formula A8. Removal of the trifluoroacetyl group of a compound of formula A8 may be accomplished by the action of potassium carbonate or TEA in the presence of an alcoholic solvent such as, methanol, to afford a compound of formula A9. A compound of formula A9 may be acylated with a carboxylic acid or acid chloride of formula A10, wherein Q is hydroxy or chloride, respectively. Appropriate coupling conditions when using a compound of formula A10 (wherein Q is OH) include a coupling agent such as, HATU, DCC, EDC, HBTU, PyBrOP, and the like; and a base such as, DIPEA, to afford a compound of formula (I). When the acylation is effected by the addition of the corresponding acid chloride, the addition of a non-nucleophilic base such as pyridine affords a compound of formula (I).

Scheme B illustrates an alternate route for the synthesis compounds of formula (I), wherein Y and Z are as defined herein.

Scheme B

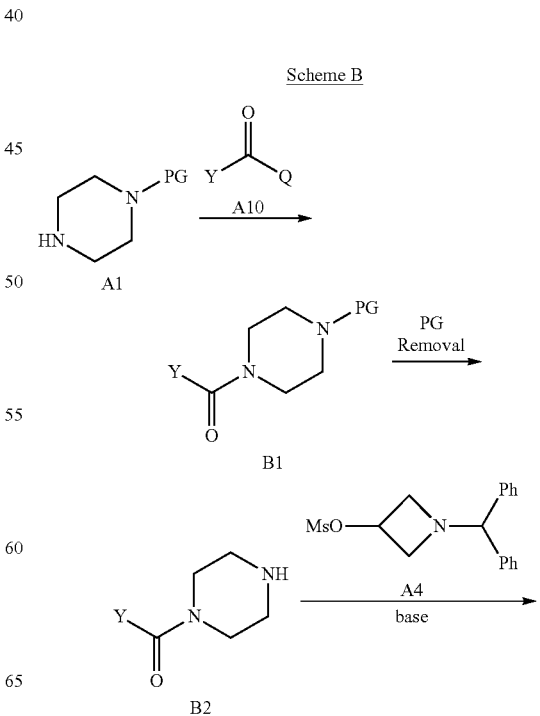

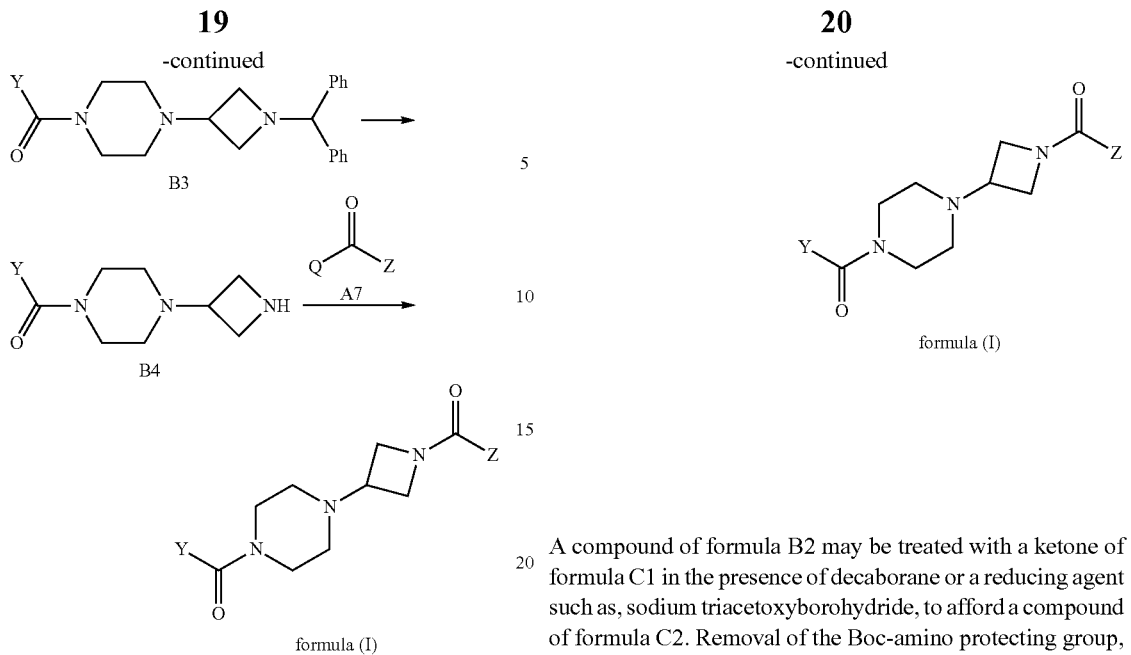

A compound of formula A1 may be acylated with a compound of formula A10 using methods and reagents previously described in Scheme A to afford a compound of formula B1. Upon conventional removal of protecting group PG, a compound of formula B2 may be treated with a compound of formula A4 in the presence of a hindered amine base such as, DIPEA, using the methods described in Scheme A to afford a compound of formula B3. Treatment of a compound of formula B3 with 1-chloroethyl chloroformate followed by methanolysis affords the corresponding amine of formula B4. An acylation reaction with a compound of formula A7 using the methods described in Scheme A affords the corresponding compound of formula (I).

Scheme C illustrates an alternate route for the synthesis compounds of formula (I)-A, wherein Y and Z are as defined herein.

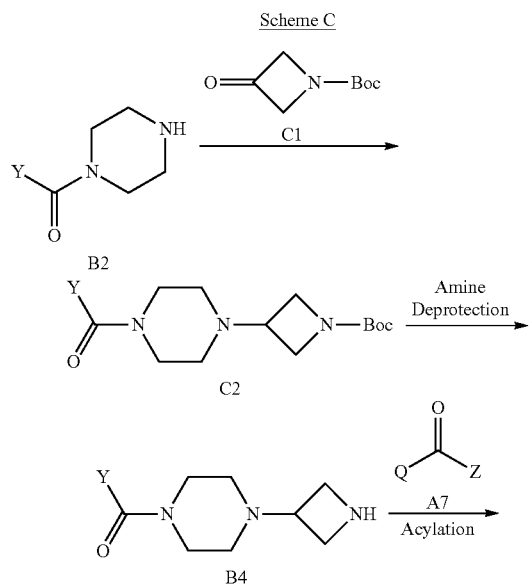

A compound of formula B2 may be treated with a ketone of formula C1 in the presence of decaborane or a reducing agent such as, sodium triacetoxyborohydride, to afford a compound of formula C2. Removal of the Boc-amino protecting group, using conventional reagents and methods, affords a compound of formula B4. Coupling with a compound of formula A7 as described herein provides a compound of formula (I).

Scheme D illustrates a route for the synthesis compounds of formula (I), wherein Y and Z are as defined herein.

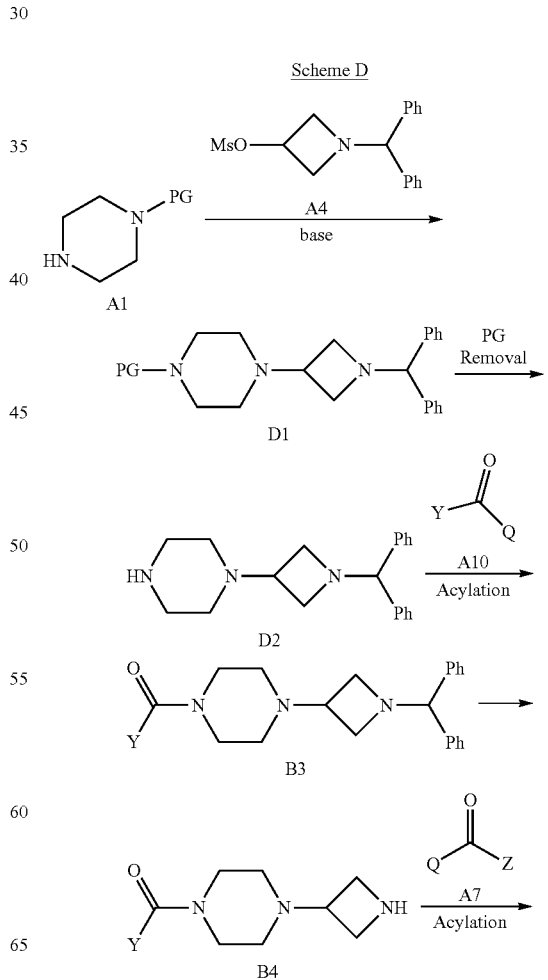

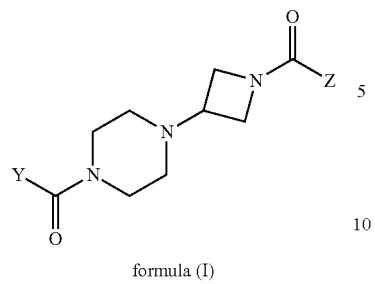

formula (I)

A compound of formula A1 may be treated with a compound of formula A4 to afford a compound of formula D1. Upon conventional removal of protecting group PG, a compound of formula D2 may be coupled with a compound of formula A10 (wherein Q is OH) in the presence of a coupling agent such as, HATU, DCC, EDC, HBTU, PyBrOP, and the like; optionally in the presence of a base such as, DIPEA, to afford a compound of formula B3. When the acylation is effected by the addition of the corresponding acid chloride, the addition of a non nucleophilic base such as pyridine affords a compound of formula B3. Removal of the benzhydryl group as described herein, followed by acylation with a compound of formula A7 affords a compound of formula (I).

One skilled in the art will recognize that the synthetic sequences of Schemes A, B, C and D may be altered so that the acylation with a compound of formula A7 precedes removal of the benzhydryl group, which is then followed by acylation with a compound of formula A10, thus reversing the order for introduction of groups Y and Z.

Scheme E illustrates a route for the synthesis compounds of formula (I)-E, wherein Y is as defined herein, and Z is a heteroaryl group, substituted with an optionally substituted phenyl or heteroaryl group, as defined herein.

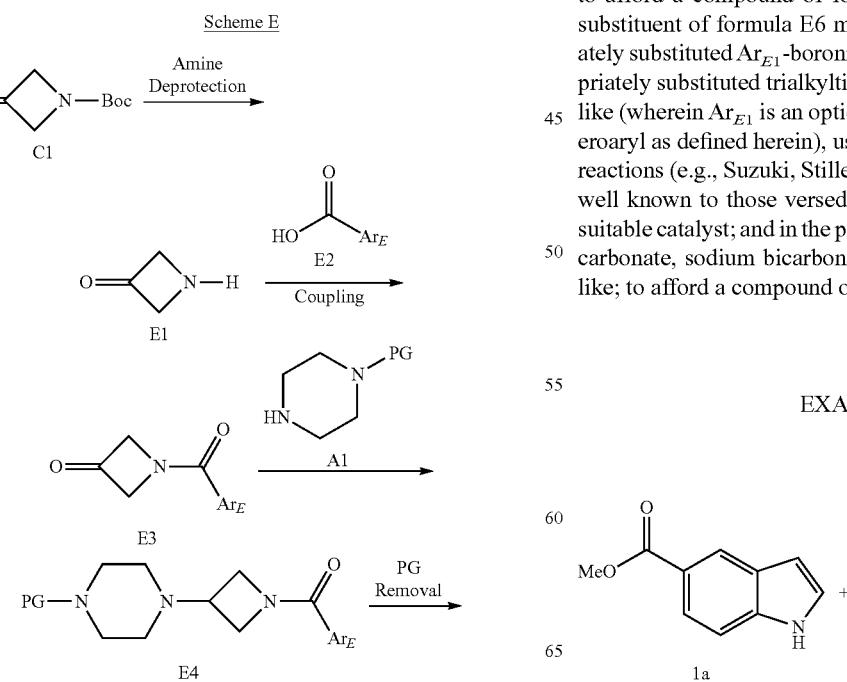

Scheme E

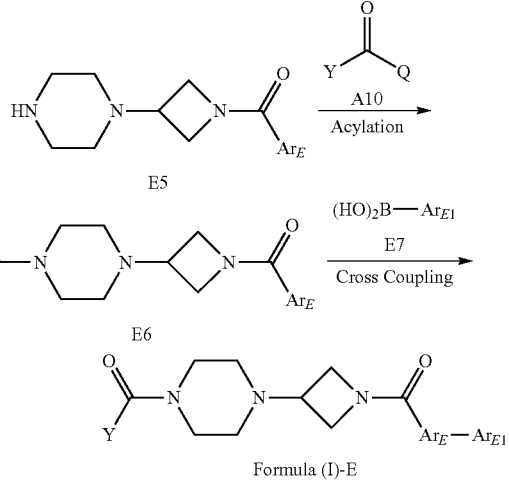

Formula (I)-E

A compound of formula C1 may be deprotected using conventional methods to afford the corresponding free amine of formula E1. Coupling with a carboxylic acid of formula E2, (wherein $Ar_E$ is a heteroaryl group, and said $Ar_E$ is substituted with one bromo, chloro, or iodo substitutent), in the presence of a coupling agent such as, HATU, DCC, EDC, HBTU, PyBrOP, and the like; optionally in the presence of a base such as, DIPEA, affords a compound of formula E3. A ketone of formula E3 may undergo a reductive amination with a compound of formula A1 in the presence of decaborane, sodium triacetoxyborohydride, and the like, to afford a compound of formula E4. Upon conventional removal of the amino protecting group PG, the free amine of formula E5 may be acylated with a compound of formula A10 as described herein to afford a compound of formula E6. The substituted $Ar_E$ substituent of formula E6 may be treated with an appropriately substituted $Ar_{E1}$-boronic acid or ester (E7), or an appropriately substituted trialkyltin reagent, trialkylsilane, and the like (wherein $Ar_{E1}$ is an optionally substituted phenyl or heteroaryl as defined herein), using one of a variety of coupling reactions (e.g., Suzuki, Stille, and Hiyama reactions) that are well known to those versed in the art; in the presence of a suitable catalyst; and in the presence of a base such as, cesium carbonate, sodium bicarbonate, potassium fluoride, and the like; to afford a compound of the formula (I)-E.

EXAMPLE 1

EXAMPLE 2

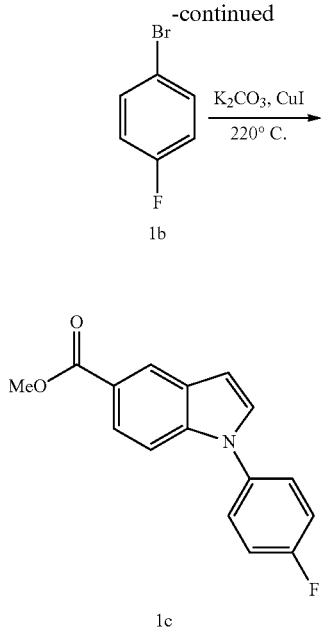
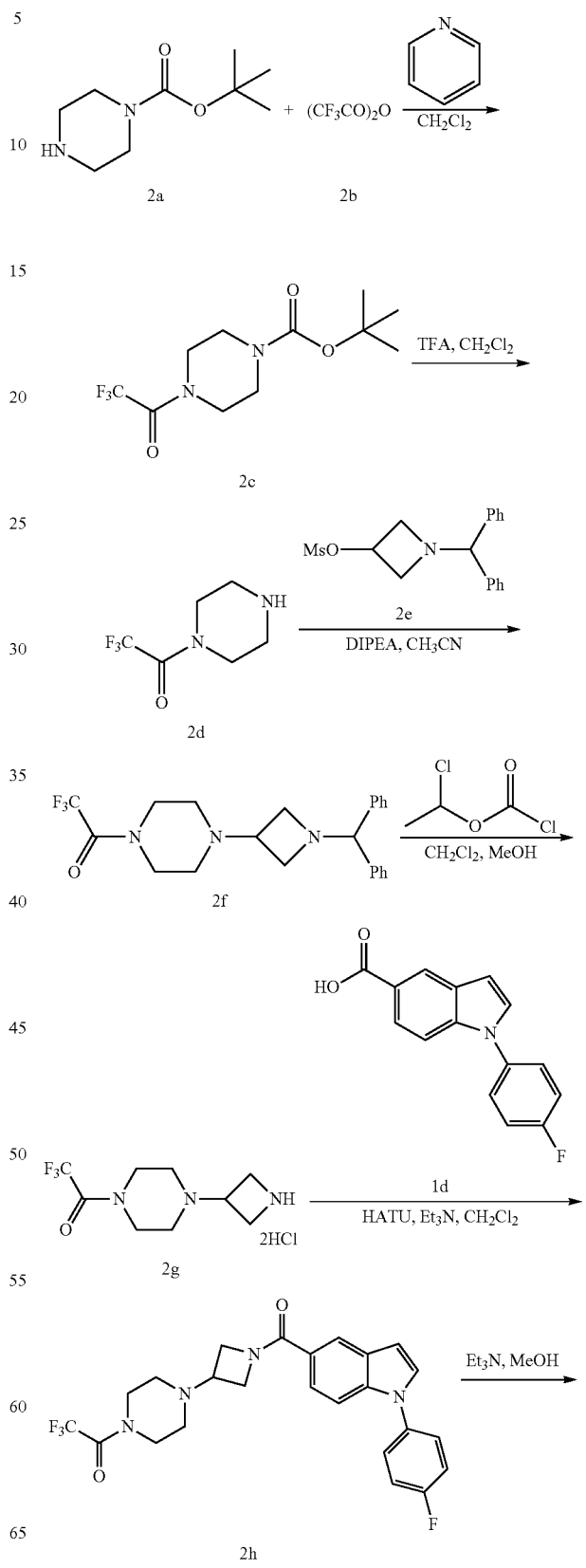

A. Methyl 1-(4-fluorophenyl)-indole-5-carboxylate, 1c. A mixture of methyl indole-5-carboxylate 1a (0.5 g, 2.85 mmol), 1-bromo-4-fluoro-benzene 1b (2 mL, 18.21 mmol), CuI (0.544 g, 2.85 mmol), and $K_2CO_3$ (0.591 g, 4.28 mmol) was heated in a microwave reactor at 220° C. for 2.5 hours. The reaction mixture was diluted with $CH_2Cl_2$ and filtered. The solution was concentrated and the residue was purified by flash column chromatography (silica gel, 15% EtOAc/heptane) to give compound 1c (0.58 g).

B. 1-(4-fluorophenyl)-indole-5-carboxylic acid, 1d. A mixture of methyl 1-(4-fluorophenyl)-indole-5-carboxylate 1c (0.58 g, 2.15 mmol) and LiOH $H_2O$ (0.36 g, 8.6 mmol) in THF (15 mL) and $H_2O$ (10 mL) was stirred at room temperature for 5 days. Aqueous 10% HCl solution was added to the reaction mixture to adjust to pH 3-4. The resulting mixture was extracted with EtOAc (2×). The organic solution was washed with aq. NaCl, dried over $Na_2SO_4$ and concentrated to give compound 1d (0.5 g).

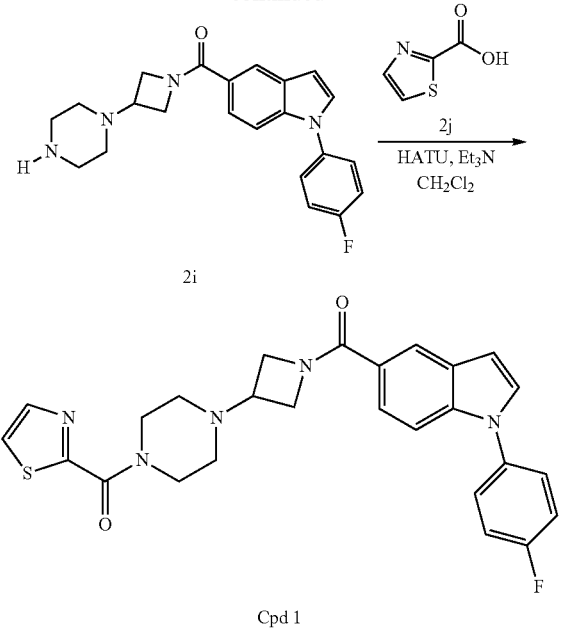

A. 4-(2,2,2-Trifluoro-acetyl)-piperazine-1-carboxylic acid tert-butyl ester, 2c. To a solution of piperazine-1-carboxylic acid tert-butyl ester (2a, 10 g, 53.69 mmol) and pyridine (8.7 mL, 107.57 mmol) in CH$_2$Cl$_2$ (100 mL) was added dropwise compound 2b (10.5 mL, 75.54 mmol) at 0° C. The mixture was stirred at 0° C. for 2 h. 2N HCl (60 mL) was added to the mixture. The organic layer was dried over MgSO$_4$, filtered, and then concentrated. The crude compound 2c was used in the next reaction without further purification. MS m/z (MH$^+$-Boc) 183.1, (MH$^+$-C$_4$H$_9$) 227.1; $^1$H NMR (300 MHz, CDCl$_3$): δ 3.45-3.7 (m, 8H), 1.5 (s, 9H).

B. 2,2,2-Trifluoro-1-piperazin-1-yl-ethanone, 2d. To a solution of compound 2c (15.15 g, 53.69 mmol) in CH$_2$Cl$_2$ (60 mL) was added trifluoroacetic acid (TFA) (18 mL) at room temperature. The mixture was stirred at room temperature for 18 h. The solvent was removed by evaporation. Ether (100 mL) was added to the residue. The resultant white solid was collected by filtration, washed with ether, and dried under vacuum. The crude compound 2d was used in the next reaction without further purification. MS m/z (M+H$^+$) 183.1.

C. 1-[4-(1-Benzhydryl-azetidin-3-yl)-piperazin-1-yl]-2,2,2-trifluoro-ethanone, 2f. To a solution of compound 2d (6 g, 32.94 mmol) and compound 2e (12.5 g, 39.38 mmol) in CH$_3$CN (60 mL) was added DIPEA (12 mL, 68.89 mmol) at room temperature. The mixture was refluxed for 2 h. The solvent was removed by evaporation and the residue was partitioned between CH$_2$Cl$_2$ and aq. NaHCO$_3$. The organic layer was washed with aq. NaHCO$_3$ (2×), then extracted with 1N HCl (2×). The aqueous layer was cooled and then the pH was adjusted with 1N NaOH until basic (pH 10). The mixture was extracted with CH$_2$Cl$_2$ (2×). The organic layer was dried over MgSO$_4$, filtered, and concentrated. Compound 2f was purified by reverse phase chromatography. MS m/z (M+H$^+$) 404.2.

D. 1-(4-Azetidin-3-yl-piperazin-1-yl)-2,2,2-trifluoro-ethanone, 2g. To a solution of compound 2f (2.11 g, 5.23 mmol) in CH$_2$Cl$_2$ (60 mL) was added 1-chloroethyl chloroformate (2.0 mL, 18.35 mmol) at 0° C. under N$_2$. The mixture was stirred at 0° C. for 90 min and then MeOH (4 mL) was added. The mixture was refluxed for 1 h. Upon cooling, Et$_2$O (50 mL) was added to the mixture. The resulting solid was collected by filtration and dried. The crude compound 2g was used in the next reaction without further purification. MS m/z (M+H$^+$) 238.1.

E. 2,2,2-Trifluoro-1-(4-(1-(1-(4-fluorophenyl)-1H-indole-5-carbonyl)azetidin-3-yl)piperazin-1-yl)ethanone, 2h. A mixture of 2 g (240 mg, 0.77 mmol), 1d (178 mg, 0.70 mmol), Et$_3$N (0.58 mL, 4.2 mmol), and HATU (294 mg, 0.77 mmol) in CH$_2$Cl$_2$ (7 mL) was stirred at room temperature for 16 h. The reaction mixture was diluted with ethyl ether, washed with aq NaHCO$_3$ and aq NaCl, dried over Na$_2$SO$_4$ and concentrated. Purification by flash column chromatography (silica gel, 3% MeOH/CH$_2$Cl$_2$) gave 2h (290 mg).

F. (1-(4-Fluorophenyl)-1H-indol-5-yl)(3-(piperazin-1-yl)azetidin-1-yl)methanone, 2i. A solution of 2h (290 mg, 0.61 mmol) in a mixture of Et$_3$N (1 mL) and MeOH (9 mL) was stirred for 4 days and concentrated to give 2i which was used in the next step without further purification.

G. 1-(4-Fluorophenyl)-5-({3-[4-(1,3-thiazol-2-ylcarbonyl)piperazin-1-yl]azetidin-1-yl}carbonyl)-1H-indole, Cpd 1. A mixture of 2i (76 mg, 0.20 mmol), 2j (34 mg, 0.26 mmol), Et$_3$N (0.08 mL, 0.6 mmol), and HATU (99 mg, 0.26 mmol) in CH$_2$Cl$_2$ (3 mL) was stirred at room temperature for 16 h. The reaction mixture was diluted with ethyl ether, washed with aq NaHCO$_3$ and aq NaCl, dried over Na$_2$SO$_4$ and concentrated. Purification by flash column chromatography (silica gel, 3% MeOH/CH$_2$Cl$_2$) gave Cpd 1. $^1$HNMR (400 MHz, CD$_3$OD): δ 8.00 (d, J=1.2 Hz, 1H), 7.88 (d, J=3 Hz, 1H), 7.55 (m, 2H), 7.46 (m, 3H), 7.34 (d, J=3 Hz, 1H), 7.27-7.21 (m, 2H), 6.74 (d, J=3 Hz, 1H), 4.52 (bs, 1H), 4.43-4.20 (m, 4H), 4.14 (m, 1H), 3.95-3.80 (m, 2H), 3.25 (m, 1H), 2.60-2.40 (m, 4H). MS m/z (M+H$^+$) 490.

EXAMPLE 3

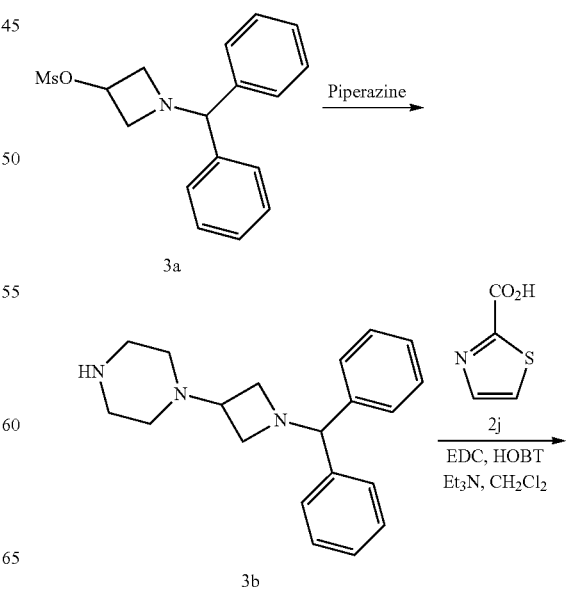

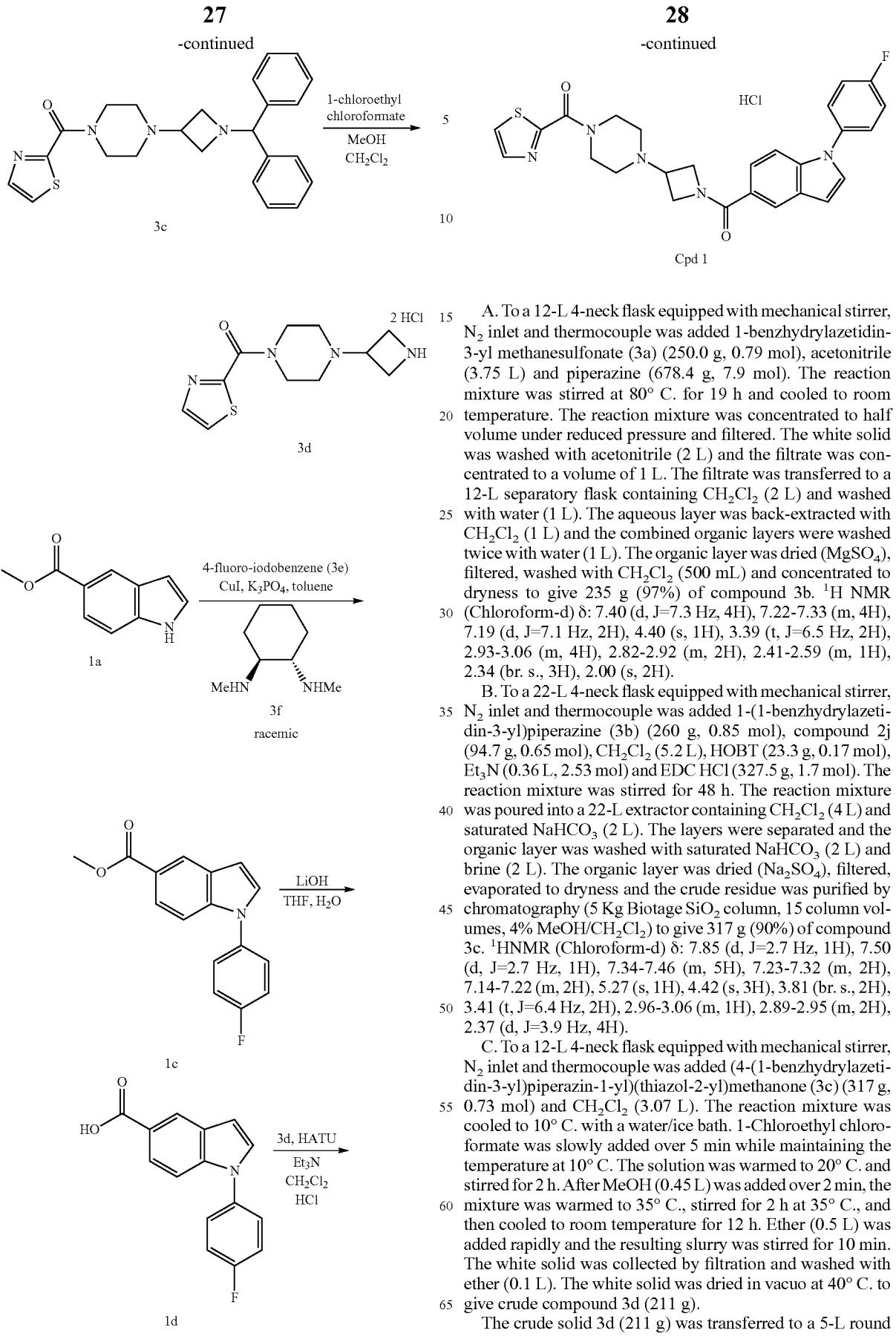

A. To a 12-L 4-neck flask equipped with mechanical stirrer, $N_2$ inlet and thermocouple was added 1-benzhydrylazetidin-3-yl methanesulfonate (3a) (250.0 g, 0.79 mol), acetonitrile (3.75 L) and piperazine (678.4 g, 7.9 mol). The reaction mixture was stirred at 80° C. for 19 h and cooled to room temperature. The reaction mixture was concentrated to half volume under reduced pressure and filtered. The white solid was washed with acetonitrile (2 L) and the filtrate was concentrated to a volume of 1 L. The filtrate was transferred to a 12-L separatory flask containing $CH_2Cl_2$ (2 L) and washed with water (1 L). The aqueous layer was back-extracted with $CH_2Cl_2$ (1 L) and the combined organic layers were washed twice with water (1 L). The organic layer was dried ($MgSO_4$), filtered, washed with $CH_2Cl_2$ (500 mL) and concentrated to dryness to give 235 g (97%) of compound 3b. $^1$H NMR (Chloroform-d) δ: 7.40 (d, J=7.3 Hz, 4H), 7.22-7.33 (m, 4H), 7.19 (d, J=7.1 Hz, 2H), 4.40 (s, 1H), 3.39 (t, J=6.5 Hz, 2H), 2.93-3.06 (m, 4H), 2.82-2.92 (m, 2H), 2.41-2.59 (m, 1H), 2.34 (br. s., 3H), 2.00 (s, 2H).

B. To a 22-L 4-neck flask equipped with mechanical stirrer, $N_2$ inlet and thermocouple was added 1-(1-benzhydrylazetidin-3-yl)piperazine (3b) (260 g, 0.85 mol), compound 2j (94.7 g, 0.65 mol), $CH_2Cl_2$ (5.2 L), HOBT (23.3 g, 0.17 mol), $Et_3N$ (0.36 L, 2.53 mol) and EDC HCl (327.5 g, 1.7 mol). The reaction mixture was stirred for 48 h. The reaction mixture was poured into a 22-L extractor containing $CH_2Cl_2$ (4 L) and saturated $NaHCO_3$ (2 L). The layers were separated and the organic layer was washed with saturated $NaHCO_3$ (2 L) and brine (2 L). The organic layer was dried ($Na_2SO_4$), filtered, evaporated to dryness and the crude residue was purified by chromatography (5 Kg Biotage $SiO_2$ column, 15 column volumes, 4% $MeOH/CH_2Cl_2$) to give 317 g (90%) of compound 3c. $^1$HNMR (Chloroform-d) δ: 7.85 (d, J=2.7 Hz, 1H), 7.50 (d, J=2.7 Hz, 1H), 7.34-7.46 (m, 5H), 7.23-7.32 (m, 2H), 7.14-7.22 (m, 2H), 5.27 (s, 1H), 4.42 (s, 3H), 3.81 (br. s., 2H), 3.41 (t, J=6.4 Hz, 2H), 2.96-3.06 (m, 1H), 2.89-2.95 (m, 2H), 2.37 (d, J=3.9 Hz, 4H).

C. To a 12-L 4-neck flask equipped with mechanical stirrer, $N_2$ inlet and thermocouple was added (4-(1-benzhydrylazetidin-3-yl)piperazin-1-yl)(thiazol-2-yl)methanone (3c) (317 g, 0.73 mol) and $CH_2Cl_2$ (3.07 L). The reaction mixture was cooled to 10° C. with a water/ice bath. 1-Chloroethyl chloroformate was slowly added over 5 min while maintaining the temperature at 10° C. The solution was warmed to 20° C. and stirred for 2 h. After MeOH (0.45 L) was added over 2 min, the mixture was warmed to 35° C., stirred for 2 h at 35° C., and then cooled to room temperature for 12 h. Ether (0.5 L) was added rapidly and the resulting slurry was stirred for 10 min. The white solid was collected by filtration and washed with ether (0.1 L). The white solid was dried in vacuo at 40° C. to give crude compound 3d (211 g).

The crude solid 3d (211 g) was transferred to a 5-L round bottom flask with a mechanical stirrer, $N_2$ inlet and thermocouple and EtOH (0.45 L) was added and the slurry was heated to 55° C. for 0.5 h. The slurry was cooled to room temperature and stirred for 1 h. The thick slurry was filtered and washed with EtOH (0.15 L). The white solid was dried in vacuo at 45° C. to give compound 3d (189 g, 79%). $^1$H NMR (MeOD) δ: 7.98 (d, J=3.2 Hz, 1H), 7.89 (d, J=3.2 Hz, 1H), 4.64-4.79 (m, 2H), 4.29-4.47 (m, 4H), 3.33-3.47 (m, 3H), 3.31 (dt, 5H).

D. To a 3-L 4-neck flask equipped with mechanical stirrer, N$_2$ inlet and thermocouple was added compound 1a (124 g, 0.71 mol), toluene (0.99 L), 4-fluoro-iodobenzene (cpd 3e, 314.27 g, 1.42 mol), racemic trans-N,N'-dimethylcyclohexane-1,2-diamine (cpd 3f, 30.2 g, 0.21 mol), copper iodide (13.48 g, 0.078 mol) and tribasic-N-hydrate potassium phosphate (330.54 g, 1.56 mol). The mixture was heated to 85° C. for 12 h. A second charge of 4-fluoro-iodobenzene (47.14 g, 0.21 mol) was added and the mixture was heated to 85° C. for 4 h. The reaction mixture was filtered through a diatomaceous earth pad and was washed with CH$_2$Cl$_2$ (2 L). The solvent was evaporated and the residue was purified by column chromatography (2.5 Kg Biotage SiO$_2$ column, 15 column volumes, 10% EtOAc/Heptane) to give 110 g (58%) of compound 1c. $^1$H NMR (Chloroform-d) δ: 8.45 (d, J=1.5 Hz, 1H), 7.92 (dd, J=8.8, 1.5 Hz, 1H), 7.41-7.50 (m, 3H), 7.34 (d, J=3.2 Hz, 1H), 7.17-7.29 (m, 1H), 6.77 (d, J=3.4 Hz, 1H), 3.94 (s, 3H).

E. To a 3-L 4-neck flask equipped with mechanical stirrer, N$_2$ inlet, condenser and thermocouple was added compound 1c (58.0 g, 0.215 mol), THF (0.58 L), deionized water (0.58 L) and lithium hydroxide (20.63 g, 0.86 mol). The reaction mixture was warmed to 55° C. for 18 h. The reaction was cooled to room temperature and the pH was adjusted to ~3 with 1M HCl (~0.8 L). A white precipitate formed during pH adjustment. The thick white slurry was filtered and washed with deionized water (0.3 L). The white solid was dried in vacuo at 45° C. to give compound 1d (53.5 g, 97%). $^1$H NMR (Chloroform-d) δ: 8.54 (s, 1H), 7.99 (d, J=8.6 Hz, 1H), 7.48 (d, J=8.8 Hz, 3H), 7.36 (d, J=2.9 Hz, 1H), 7.23-7.32 (m, 2H), 6.81 (d, 1H).

F. To a 5-L 4-neck flask equipped with mechanical stirrer, N$_2$ inlet, condenser and thermocouple was added compound 1d (105.0 g, 0.41 mol), CH$_2$Cl$_2$ (1.58 L), Et$_3$N (0.344 L, 2.47 mol), (4-(azetidin-3-yl)piperazin-1-yl)(thiazol-2-yemethanone dihydrochloride (cpd 3d, 133.8 g, 0.41 mol) and HATU (156.4 g, 0.41 mol). The reaction was stirred for 72 h at room temperature. The reaction solution was transferred to a 22-L extractor containing CH$_2$Cl$_2$ (4 L) and sat NaHCO$_3$ (2 L). The organic layer was washed with brine (2 L), dried (NaSO$_4$), filtered and evaporated to dryness. The residue was purified by column chromatography (5 Kg Biotage SiO$_2$ column, 3 column volumes CH$_2$Cl$_2$, 10 column volumes 3% MeOH/CH$_2$Cl$_2$) to give 189 g (94%) of compound 1 as its free base. $^1$H NMR (MeOD) δ: 7.99 (s, 1H), 7.93 (d, J=3.4 Hz, 1H), 7.81 (d, J=3.2 Hz, 1H), 7.44-7.62 (m, 5H), 7.23-7.39 (m, 2H), 6.77 (d, J=3.4 Hz, 1H), 4.43-4.53 (m, 1H), 4.39 (br. s., 1H), 4.17-4.34 (m, 2H), 4.06 (dd, J=10.0, 4.9 Hz, 1H), 3.80 (br. s., 1H), 3.28-3.38 (m, 2H), 3.18-3.28 (m, 1H), 2.50 (br. s., 4H).

To a 5-L 4-neck flask equipped with mechanical stirrer, N$_2$ inlet and thermocouple was added crude compound 1 free base (147.6 g, 0.301 mol) and dichloromethane (0.738 L). 1.0 M HCl (0.301 L) was added over 5 min. After 1 h, Et$_2$O (1.476 L) was added over 5 min. The white slurry was filtered, washed with Et$_2$O (0.1 L) and dried in vacuo at 45° C. to give compound 1 (139 g, 88%) as its hydrochloride salt.

To a 5-L 4-neck flask equipped with a mechanical stirrer, N$_2$ inlet, condenser and thermocouple was added the hydrochloride salt of compound 1 (139 g, 0.264 mol) and a 1:1 mixture of MeOH and EtOH (1.112 L). The slurry was stirred at 70° C. for 3 h and allowed to cool to room temperature. The flask was placed in an ice bath for 2 h and the white slurry was filtered in a medium sintered glass funnel and washed with a 1:1 EtOH and MeOH (100 mL) solution. The cake was placed in a vacuum oven at 50° C. for 2 days. The material was collected to give 127 g (91.3%) of purified compound 1. $^1$H NMR (DMSO-d$_6$) δ: 12.57-12.97 (m, 1H), 8.11 (d, J=3.2 Hz, 1H), 8.06 (d, J=3.2 Hz, 1H), 8.01 (s, 1H), 7.76 (d, J=3.2 Hz, 1H), 7.61-7.70 (m, 2H), 7.50-7.57 (m, 2H), 7.45 (t, J=8.7 Hz, 2H), 6.82 (d, J=3.2 Hz, 1H), 5.63 (br. s., 1H), 4.38-4.87 (m, 4H), 4.05-4.37 (m, 3H), 3.51-3.95 (m, 4H), 2.93-3.28 (m, 2H);

Elemental Analysis $C_{26}H_{24}F_1N_5O_2S \cdot 1.06HCl \cdot 0.04H_2O \cdot 0.45C_2H_6O_1$ Theory: % C=59.07; % H=5.11; % N=13.14; % F=3.47; % S=5.86; % Cl=6.48

Found: % C=58.87; % H=4.77; % N=12.80; % F=3.77; % S=5.92; % Cl=6.53%

% H$_2$O found=<0.1%

% Ash=<0.1.

BIOLOGICAL EXAMPLES

In Vitro Methods

EXAMPLE 1

MGL Enzyme Activity Assay

All rate-based assays were performed in black 384-well polypropylene polymerase chain reaction (PCR) microplates (Abgene) in a total volume of 30 μL. Substrate 4-methylumbelliferyl butyrate (4MU-B; Sigma) and either purified mutant MGL (mut-MGLL 11-313 L179S L186S) or purified wild type MGL (wt-MGLL 6H-11-313) were diluted separately into 20 mM PIPES buffer (pH=7.0), containing 150 mM NaCl and 0.001% Tween 20. Compounds of formula (I) were pre-dispensed (50 nL) into the microplate using a liquid handling dispenser prior to adding 4MU-B (25 μL of 1.2× solution to a final concentration of 10 μM) followed by enzyme (5 μL of a 6× solution to a final concentration of 5 nM) to initiate the reaction. Final compound concentrations ranged from 17 to 0.0003 μM. The fluorescence change due to 4MU-B cleavage was monitored with excitation and emission wavelengths of 335 and 440 nm, respectively, and a bandwidth of 10 nm (Safire$^2$, Tecan) at 37° C. for 5 min.

The IC$_{50}$ values for compounds of formula (I) were determined using a spreadsheet, i.e., Excel® from Microsoft, from a fit of the equation to the concentration-response plot of the fractional activity as a function of inhibitor concentration.

TABLE 1

| Biological Data | | |
| --- | --- | --- |
| Cpd | MGL mutant inh IC$_{50}$ (μM) | MGL wild type inh IC$_{50}$ (μM) |
| 1 | <0.005 | <0.005 |

EXAMPLE 2

2-AG Accumulation Assay

To measure the accumulation of 2-AG due to inhibition of MGL, one g rat brain was homogenized using a Polytron homogenizer (Brinkmann, PT300) in 10 mL of 20 mM HEPES buffer (pH=7.4), containing 125 mM NaCl, 1 mM EDTA, 5 mM KCl and 20 mM glucose. Compounds of formula (I) (10 µM) were pre-incubated with rat brain homogenate (50 mg). After a 15-min incubation time at 37° C., $CaCl_2$ (final concentration=10 mM) was added and then incubated for 15 min at 37° C. in a total volume of 5 mL. The reactions were stopped with 6 mL organic solvent extraction solution of 2:1 chloroform/methanol. Accumulated 2-AG in the organic phase was measured by a HPLC/MS method, according to the following equation:

percent vehicle=(2-AG accumulation in the presence of compound/2-AG accumulation in vehicle)×100.

TABLE 2

| | Biological Data | | | |
|---|---|---|---|---|
| | Rat Brain 2AG % VehCntrl | | | |
| Cpd | (%) @ 0.01 µM | (%) @ 0.1 µM | (%) @ 1 µM | (%) @ 10 µM |
| 1 | | 463 | 2081 | 2182 |

EXAMPLE 3

MGL ThermoFluor® Assay-mutant

The ThermoFluor (TF) assay is a 384-well microplate-based binding assay that measures thermal stability of proteins[1,2]. The experiments were carried out using ThermoFluor instruments available from Johnson & Johnson Pharmaceutical Research & Development, LLC. TF dye used in all experiments was 1,8-ANS (Invitrogen: A-47). Final TF assay conditions used for MGL studies were 0.07 mg/ml of mutant MGL, 100 µM ANS, 200 mM NaCl, 0.001% Tween-20 in 50 mM PIPES (pH=7.0).

Screening compound plates contained 100% DMSO compound solutions at a single concentration. For follow-up concentration-response studies, compounds were arranged in a pre-dispensed plate (Greiner Bio-one: 781280), wherein compounds were serially diluted in 100% DMSO across 11 columns within a series. Columns 12 and 24 were used as DMSO reference and contained no compound. For both single and multiple compound concentration-repsonse experiments, the compound aliquots (46 mL) were robotically predispensed directly into 384-well black microplates (Abgene: TF-0384/k) using the Hummingbird liquid handler. Following compound dispension, protein and dye solutions were added to achieve the final assay volume of 3 µL. The assay solutions were overlayed with 1 µL of silicone oil (Fluka, type DC 200: 85411) to prevent evaporation.

Bar-coded microplates were robotically loaded onto a thermostatically controlled PCR-type thermal block and then heated from 40 to 90° C. degrees at a ramp-rate of 1° C./min for all experiments. Fluorescence was measured by continuous illumination with UV light (Hamamatsu LC6), supplied via fiber optics and filtered through a band-pass filter (380-400 nm; >6 OD cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. A single image with 20-sec exposure time was collected at each temperature, and the sum of the pixel intensity in a given area of the assay plate was recorded vs temperature and fit to standard equations to yield the $T_m^1$.

1. Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) *J Biomol Screen* 6, 429-40.
2. Matulis, D., Kranz, J. K., Salemme, F. R., and Todd, M. J. (2005) *Biochemistry* 44, 5258-66.

TABLE 3

| Biological Data | |
|---|---|
| Cpd | MGL mutant ThermoFluor Kd (µM) |
| 1 | 0.0014 +/− 0.0006 |

In Vivo Methods

Genetic and environmental factors play a role in the development of obesity and diet is one of the main environmental factors that contribute to this disease. Human studies have shown that increased fat intake is associated with body weight gain that can lead to obesity and other related metabolic diseases. Rodent models fed high-fat diets are therefore useful tools for studying obesity as they will readily gain weight. (Buettner R. et al. *Obesity* (Silver Spring), 2007, 15, 798-808; van Heek, M. et al. *J Clin Invest*, 1997, 99, 385-390). In addition, the high-fat diet-fed rodent model is a useful model to study impaired glucose tolerance and early type 2 diabetes (Soerhede-Winzell, M., *Diabetes*, December 2004, 53(3), S215-S219). This model has been used for studies on pathophysiology and development of new treatments for diabetes, including DPP-IV inhibition and PPAR agonism, both of which were associated with improved insulin secretion in rodents and humans.

EXAMPLE 4

Effect on Food Intake after Food Deprivation in Rats

In rats, food deprivation or restriction is a standard method for inducing increased food intake. In other words, depriving the rats of food and then subsequently presenting them with food results, predictably in over-eating (also referred to as rebound hyperphagia). To study the effect of compounds of formula (I) on feeding behavior, rats were treated after food deprivation.

Adult, male Sprague-Dawley rats were single-housed on a 12 h light/dark cycle and received food and water ad libitum, except where otherwise indicated. Rats were allowed to acclimate to the housing room for at least 1 week prior to testing. One day prior to treatment, each rat was transferred to a new cage that was free of bedding and contained a wire grid floor, and all food was removed. Rats were fasted for 18 h before treatment. Rats were divided into two groups (N=6/group) and received either a compound of formula (I) at 30 mg/kg, p.o. or vehicle. At dosing, all rats received a pre-measured amount of standard rodent chow. After 30 min, the food was re-weighed to determine the amount consumed.

Results of the Food Intake After Food Deprivation study are shown in the table 4 below and reveal that vehicle-treated rats ate more food after food deprivation than rats treated with a compound of formula (I).

TABLE 4

| Group | Food Intake (g of food over 30 min) |
|---|---|
| Vehicle | 3.93 ± 0.37 |
| Cpd 1 | 1.60 ± 1.02 |

EXAMPLE 5

5-Day Repeat Dose with Weight Monitoring in Rats

Male and Female rats, strain CD(SD)IGS (Charles River Laboratories International, Inc., MA) of 8 weeks of age were individually housed and maintained on a 12-hr light/dark cycle. Rats were fed ad libitum with a standard diet (Rodent Diet 5001, PMI Nutrition International, Indiana). A compound of formula (I) was administered orally by metal gavage needle to male and female rats (5 per group) for 5 consecutive days at 0, 15, and 50 mg/kg/day. Rats were weighed predose and on days 1 and 4. Clinical observations were recorded prior to dosing, at 2 hours post-dose each day. Rats were fasted overnight on Day 4 and blood was collected on Day 5 from the retro-orbital sinus following anesthesia with a 70/30% carbon dioxide/oxygen mixture. Blood was collected into tubes containing tripotassium EDTA for hematology panel and no additive for serum chemistry determinations. Rats were euthanized by $CO_2$ inhalation and thoracic and abdominal cavities were examined and weights of liver determined.

Results of the 5-Day Repeat Dose Investigation of a Compound of Formula (I) with Weight Monitoring are shown in Table 5, below, and revealed dose-dependent decreased mean body weights for males and females at 50 mg/kg. Minimal changes in hematology and chemistry parameters were within expected biological variation. Compound-related elevated serum cholesterol levels were seen in one or both sexes at ≥15 mg/kg, with no anatomic pathology correlation. Examination of abdominal cavity at necropsy revealed red pinpoint discoloration in the glandular area of the stomach in 2 of 5 males administered 15 mg/kg, 1 of 5 males and 3 of 5 females administered 50 mg/kg.

TABLE 5

Biological Data

| | | 0 mg/kg/day Mean value | 15 mg/kg/day Mean value | 50 mg/kg/day Mean value |
|---|---|---|---|---|
| Male | Day −1 | 274.80 +/− 8.09 | 273.34 +/− 4.80 | 272.66 +/− 6.92 |
| | Day 4 | 308.66 +/− 10.43 | 301.94 +/− 7.52 | 278.78 +/− 6.95 |
| | Change | 33.86 +/− 3.35 | 28.60 +/− 2.90 | 6.10 +/− 3.56* |
| Female | Day −1 | 203.88 +/− 5.73 | 203.86 +/− 6.13 | 199.16 +/− 5.66 |
| | Day 4 | 227.66 +/− 7.5 | 226.98 +/− 10.29 | 207.70 +/− 4.96 |
| | Change | 23.78 +/− 4.04 | 23.12 +/− 4.63 | 8.54 +/− 2.32 |

*p > 0.05

EXAMPLE 6

5-Day Repeat Dose with Weight Monitoring in Dogs

Male and female beagle dogs, 15 months of age, were individually housed and maintained on a 12-hourlight/dark cycle. Dogs were given 300 g/day of Advanced Protocol™ Non-Certified High Density Canine Diet 5L18 (pMfID Nutrition International). Food was provided 0.5 to 2 hours postdose, except on days of toxicokinetic blood sampling when food was provided after the 4 hour time point. Canned food was supplemented beginning on day 3. A compound of formula (I) was administered orally via gavage using a stomach tube once daily (initiating on Day 0) to male and female dogs (1 each per dose) for 5 consecutive days at 0, 5, 15 and 45 mg/kg/day. Dogs were weighed on Day-1 and Day 5 prior to necropsy. Food consumption was determined 3 days predose and then daily. Body temperature was measured at 0 (predose), 4 and 24 hours on Days 0 and 4. Clinical observations were recorded predose and 2 hours postdose daily. Dogs were fasted overnight prior to blood collection. Blood was collected from all dogs predose on Day-8 and prior to dosing on Day 4 from the jugular vein. Blood was collected into tubes containing tripotassium EDTA for hematology and no additive for serum chemistry determinations. At necropsy, the thoracic and abdominal cavities were examined.

In all groups treated with a compound of formula (I), a decrease in body weight, little or no food consumption, absent and/or decreased feces on most days, and sporadic emesis were observed and are shown in Table 6, below. In addition, a decrease in body temperature (4 hours postdose on Day 0), was observed. A stained urogenital area was also observed in all dogs administered 15 and 45 mg/kg. There were no compound-related changes in clinical pathology parameters, nor were there any changes noted at gross necropsy.

TABLE 6

Biological Data

| | Daily Dose of Cpd 1 (mg/kg) | | | | | | | |
|---|---|---|---|---|---|---|---|---|
| | 0 (Control) | | 5 | | 15 | | 45 | |
| | No. of dogs | | | | | | | |
| | M:1 | F:1 | M:1 | F:1 | M:1 | F:1 | M:1 | F:1 |
| Body Weight Change | −0.13 | −0.13 | −1.10 | −0.90 | −0.74 | — | −0.78 | −1.28 |
| | Clinical Observations | | | | | | | |
| Feces, decrease | — | — | 1 | 1 | 1 | 1 | 1 | 1 |
| Feces, absent | — | — | 1 | 1 | 1 | 1 | 1 | 1 |
| Emesis | — | — | 1 | 1 | 1 | 1 | 1 | 1 |
| Stained urogenital area | — | — | — | — | 1 | 1 | 1 | 1 |
| Food Consumption | — | — | ↓ | ↓ | ↓ | ↓ | ↓ | ↓ |
| Body Temperature Change | — | — | −3.4 | −3.2 | — | −1.6 | −1.9 | — |

<sup>a</sup>Estimated dry food consumption for Days 1-3 was 0% for all dogs on all days (except for the high dose male that ate 25% on Day 3). Day 3 food consumption of supplemental canned food was 0% for both dogs administered 5 mg/kg and 100% for dogs administered 15 and 45 mg/kg.
— No noteworthy findings While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A method of reducing food consumption of a subject comprising administering to the subject in need thereof, a therapeutically effective amount of Compound 1
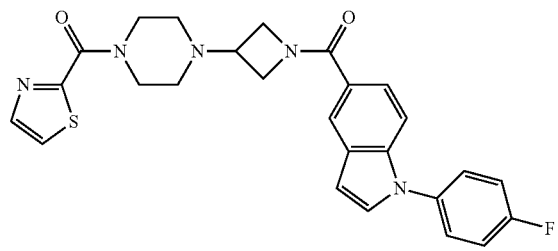 [SMILES: O=C(c1ccc2c(ccn2-c2ccc(F)cc2)c1)N1CC(N2CCN(C(=O)c3nccs3)CC2)C1]
or a pharmaceutically acceptable salt thereof.
2. A method of reducing food consumption of a subject, comprising administering to a subject in need thereof, a pharmaceutical composition comprising a pharmaceutically acceptable carrier and a therapeutically effective amount of
(Compound 1)
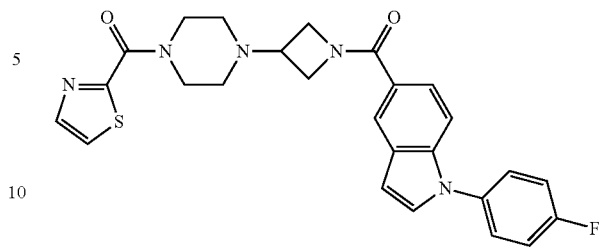
r a pharmaceutically acceptable salt thereof.
\* \* \* \* \*